US007620144B2

(12) United States Patent
Bodduluri

(10) Patent No.: US 7,620,144 B2
(45) Date of Patent: Nov. 17, 2009

(54) PARALLEL STEREOVISION GEOMETRY IN IMAGE-GUIDED RADIOSURGERY

(75) Inventor: Mohan Bodduluri, Palo Alto, CA (US)

(73) Assignee: Accuray Incorporated, Sunnyvale, CA (US)

( * ) Notice: Subject to any disclaimer, the term of this patent is extended or adjusted under 35 U.S.C. 154(b) by 56 days.

(21) Appl. No.: 11/478,047

(22) Filed: Jun. 28, 2006

(65) Prior Publication Data

US 2008/0002809 A1   Jan. 3, 2008

(51) Int. Cl.
*A61B 6/02* (2006.01)
*A61N 5/10* (2006.01)

(52) U.S. Cl. ........................................ 378/41; 378/65
(58) Field of Classification Search ................ 378/9, 378/41, 62, 64, 65, 4, 19
See application file for complete search history.

(56) References Cited

U.S. PATENT DOCUMENTS

| 4,807,163 | A | | 2/1989 | Gibbons |
| 4,980,971 | A | | 1/1991 | Bartschat et al. |
| 5,078,140 | A | | 1/1992 | Kwoh |
| 5,230,623 | A | | 7/1993 | Guthrie et al. |
| 5,333,107 | A | * | 7/1994 | Grangeat et al. .............. 378/19 |
| 5,901,199 | A | | 5/1999 | Murphy et al. |
| 6,307,914 | B1 | | 10/2001 | Kunieda et al. |
| 6,434,416 | B1 | | 8/2002 | Mizoguchi et al. |
| 6,484,049 | B1 | | 11/2002 | Seeley et al. |
| 6,917,702 | B2 | | 7/2005 | Beardsley |
| 7,085,343 | B2 | * | 8/2006 | Shinno et al. .................. 378/9 |
| 7,158,607 | B2 | * | 1/2007 | Dilmanian et al. ............ 378/64 |
| 7,277,120 | B2 | | 10/2007 | Gere et al. |
| 7,453,984 | B2 | * | 11/2008 | Chen et al. .................... 378/65 |
| 2007/0078466 | A1 | | 4/2007 | Bodduluri et al. |
| 2007/0106306 | A1 | | 5/2007 | Bodduluri et al. |
| 2007/0106307 | A1 | | 5/2007 | Bodduluri et al. |
| 2008/0004603 | A1 | | 1/2008 | Larkin et al. |

OTHER PUBLICATIONS

Coste-Manière, È., "Robotic whole body stereotactic radiosurgery: clinical advantages of the CyberKnife® integrated system", The International Journal of Medical Robotics+Computer Assisted Surgery, 2005, wvvw.roboticpublications.com, pp. 28-39.
International Search Report and Written Opinion of the International Searching Authority, PCT/US07/12824 filed May 30, 2007, mailed Aug. 25, 2008.
International Preliminary Report on Patentability, PCT/US2007/012824 filed May 30, 2007, mailed Jan. 15, 2009.
Kurt Konolige and David Beymer, SRI International, "SRI Small Vision System", User's Manual Software version 3.2g, Nov. 2004, 86 pages.

(Continued)

*Primary Examiner*—Irakli Kiknadze
(74) *Attorney, Agent, or Firm*—Blakely, Sokoloff, Taylor & Zafman LLP

(57) ABSTRACT

A method and apparatus in an image-guided radiation treatment system for determining an in-treatment 3-D position of a patient and for registering the 3-D in-treatment position of the patient with a pre-treatment 3-D scan of the patient.

28 Claims, 9 Drawing Sheets

OTHER PUBLICATIONS

David A. Forsyth, Jean Ponce, "Computer Vision, A Modern Approach", 2003, Cover page, publication page, and Chapters 10 and 11, pp. 215-250.

John Iselin Woodfill, Gaile Gordon, Dave Jurasek, Terrance Brown, Ron Buck, "The Tyzx DeepSea G2 Vision System, A Taskable, Embedded Stereo Camera", Proceedings of the IEEE Computer Society Workshop on Embedded Computer Vision, Conference on Computer Vision and Pattern Recognition, Jun. 2006, pp. 1-7.

John Iselin Woodfill, Gaile Gordon, Ron Buck, "Tyzx DeepSea High Speed Stereo Vision System", Proceedings of the IEEE Computer Society Workshiop on Real Time 3-D Sensors and Their Use, Conference on Computer Vision and Pattern Recognition, Jun. 2004, pp. 1-5.

J.B. Antoine Maintz et al., "A Survey of Medical Image Registration", Medical Image Analysis, (1998), vol. 2, No. 1, pp. 1-37, Oxford University Press.

Ramesh Jain, "Machine Vision", Copyright 1995, Chapters 11-12, pp. 86 total, McGraw-Hill.

Graeme P. Penney et al., "A Comparison of Similarity Measures for Use in a 2-D-3-D Medical Image Registration", IEEE Transactions on Medical Imaging, vol. 17, No. 4, Aug. 1998, pp. 586-595.

* cited by examiner

PARALLEL STEREOVISION GEOMETRY IN IMAGE-GUIDED RADIOSURGERY

TECHNICAL FIELD

Embodiments of the invention relate to the field of medical imaging and, in particular, to parallel stereovision in image-guided radiation treatment systems.

BACKGROUND

Radiosurgery and radiotherapy systems are radiation treatment systems that use external radiation beams to treat pathological anatomies (e.g., tumors, lesions, vascular malformations, nerve disorders, etc.) by delivering a prescribed dose of radiation (e.g., X-rays or gamma rays) to the pathological anatomy while minimizing radiation exposure to surrounding tissue and critical anatomical structures (e.g., the spinal chord). Both radiosurgery and radiotherapy are designed to necrotize the pathological anatomy while sparing healthy tissue and the critical structures. Radiotherapy is characterized by a low radiation dose per treatment, and many treatments (e.g., 30 to 45 days of treatment). Radiosurgery is characterized by a relatively high radiation dose in one, or at most a few, treatments.

In both radiotherapy and radiosurgery, the radiation dose is delivered to the site of the pathological anatomy from multiple angles. As the angle of each radiation beam is different, each beam can intersect a target region occupied by the pathological anatomy, while passing through different regions of healthy tissue on its way to and from the target region. As a result, the cumulative radiation dose in the target region is high and the average radiation dose to healthy tissue and critical structures is low. Radiotherapy and radiosurgery treatment systems can be classified as frame-based or image-guided.

In frame-based radiosurgery and radiotherapy, a rigid and invasive frame is fixed to the patient to immobilize the patient throughout a diagnostic imaging and treatment planning phase, and a subsequent treatment delivery phase. The frame is fixed on the patient during the entire process. Image-guided radiosurgery and radiotherapy (IGR) eliminate the need for invasive frame fixation by tracking and correcting for patient movement during treatment.

Image-guided radiotherapy and radiosurgery systems may be classified as gantry-based or robotic-based. In gantry-based systems, the radiation source is attached to a gantry that moves around a center of rotation (isocenter) in a single plane. Each time a radiation beam is delivered during treatment, the axis of the beam passes through the isocenter. In some gantry-based systems, known as intensity modulated radiation therapy (IMRT) systems, the cross-section of the beam is shaped to conform the beam to the pathological anatomy under treatment. In robotic-based systems, the radiation source is not constrained to a single plane of rotation.

In some image-guided systems, patient tracking during treatment is accomplished by registering 2-D in-treatment X-ray images of the patient (indicating where the patient is) to 2-D reference projections of one or more pre-treatment 3-D volume studies of the patient (indicating where the patient should be to match the treatment plan), and changing the position of the patient or the radiation source to correct for differences between the two sets of images. The pre-treatment 3-D volume studies may be computed tomography (CT) scans, magnetic resonance imaging (MRI) scans, positron emission tomography (PET) scans or the like.

The reference projections (reference images), known as digitally reconstructed radiographs (DRRs), are generated using ray-tracing algorithms that replicate the known geometry of the in-treatment X-ray imaging system to produce images that have the same scale and orientation as the in-treatment X-ray images. Typically, the in-treatment X-ray system images the patient using two X-ray sources and two X-ray cameras subtending large angles (e.g., 90 degrees) at the patient. This approach maximizes the sensitivity of the individual in-treatment X-ray images to patient movement, but it can produce two very dissimilar X-ray images as illustrated in FIG. 1. In FIG. 1, an anatomical feature (e.g., a bone) is imaged with two X-ray sources and two X-ray cameras separated by 90 degrees. In one camera, the length and width of the bone is imaged, while in the other camera, the cross-section of the bone is imaged. The two X-ray images are very dissimilar, requiring a separate DRR for registration with each X-ray image before the location of the patient can be determined and matched to the pre-treatment plan.

BRIEF DESCRIPTION OF THE DRAWINGS

The present invention is illustrated by way of example, and not by limitation, in the figures of the accompanying drawings in which.

DETAILED DESCRIPTION

Figure 1:
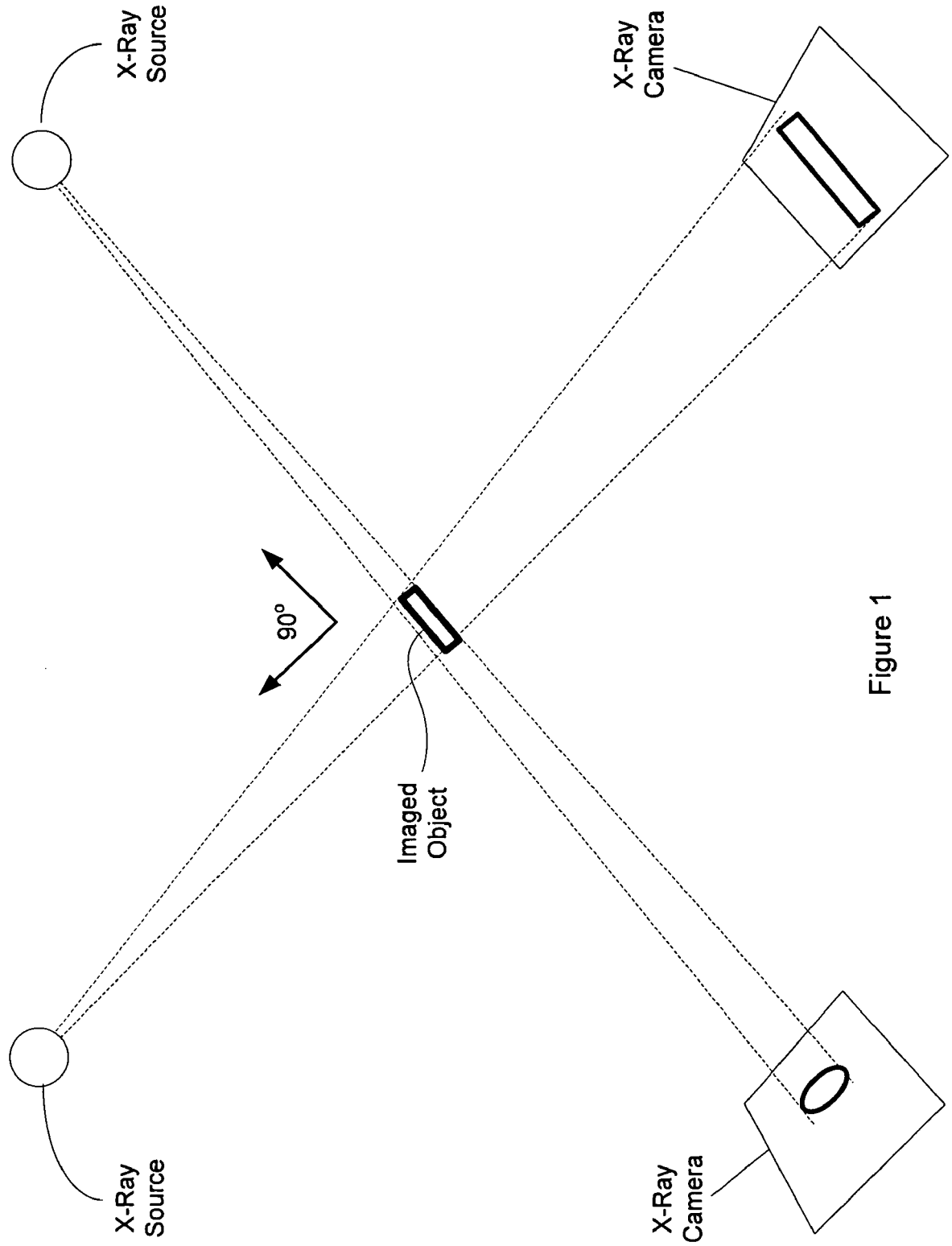
FIG. 1 illustrates wide-angle X-ray imaging.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. The term "coupled" as used herein, may mean directly coupled or indirectly coupled through one or more intervening components or systems. The term "X-Ray image" as used herein may mean a visible X-ray image (e.g., displayed on a video screen) or a digital representation of an X-ray image (e.g., a file corresponding to the pixel output of an X-ray detector). The term "in-treatment image" as used herein may refer to images captured at any point in time during a treatment delivery phase of a radiosurgery or radiotherapy procedure, which may include times when the radiation source is either on or off. The term IGR as used herein may refer to image-guided radiotherapy, image-guided radiosurgery or both.

Unless stated otherwise as apparent from the following discussion, it will be appreciated that terms such as "processing," "generating," "determining," "computing," "locating," "tracking" or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage, transmission or display devices. Embodiments of the method described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

Methods and apparatus are described for tracking patient movement during image-guided radiotherapy and/or radiosurgery by using parallel stereovision geometry to register the in-treatment position of the patient with pre-treatment 3-D volume studies. In the following descriptions of embodiments of the invention, X-ray imaging may be used as an exemplary imaging modality for 2-D in-treatment imaging. Similarly, CT scans may be used as an exemplary imaging modality for 3-D pre-treatment diagnosis and treatment planning studies. Those skilled in the art will understand that other 3-D imaging modalities (e.g., MRI, PET, 3-D ultrasound) and other 2-D imaging modalities (e.g., fluoroscopy) may be used to equal effect in other embodiments.

Figure 2A:
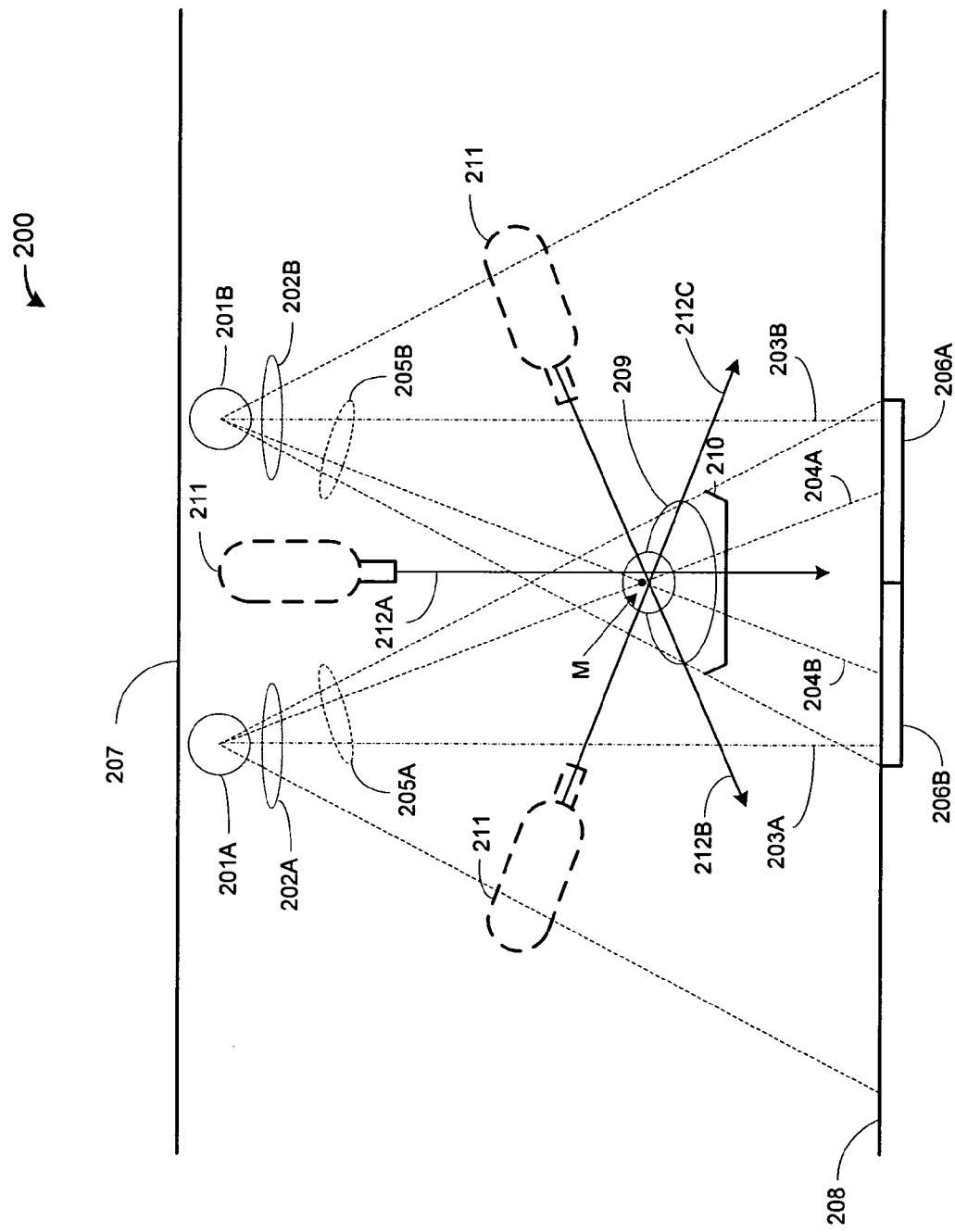
FIG. 2A illustrates one embodiment of a non-isocentric image-guided radiation treatment system.
Figure 2B:
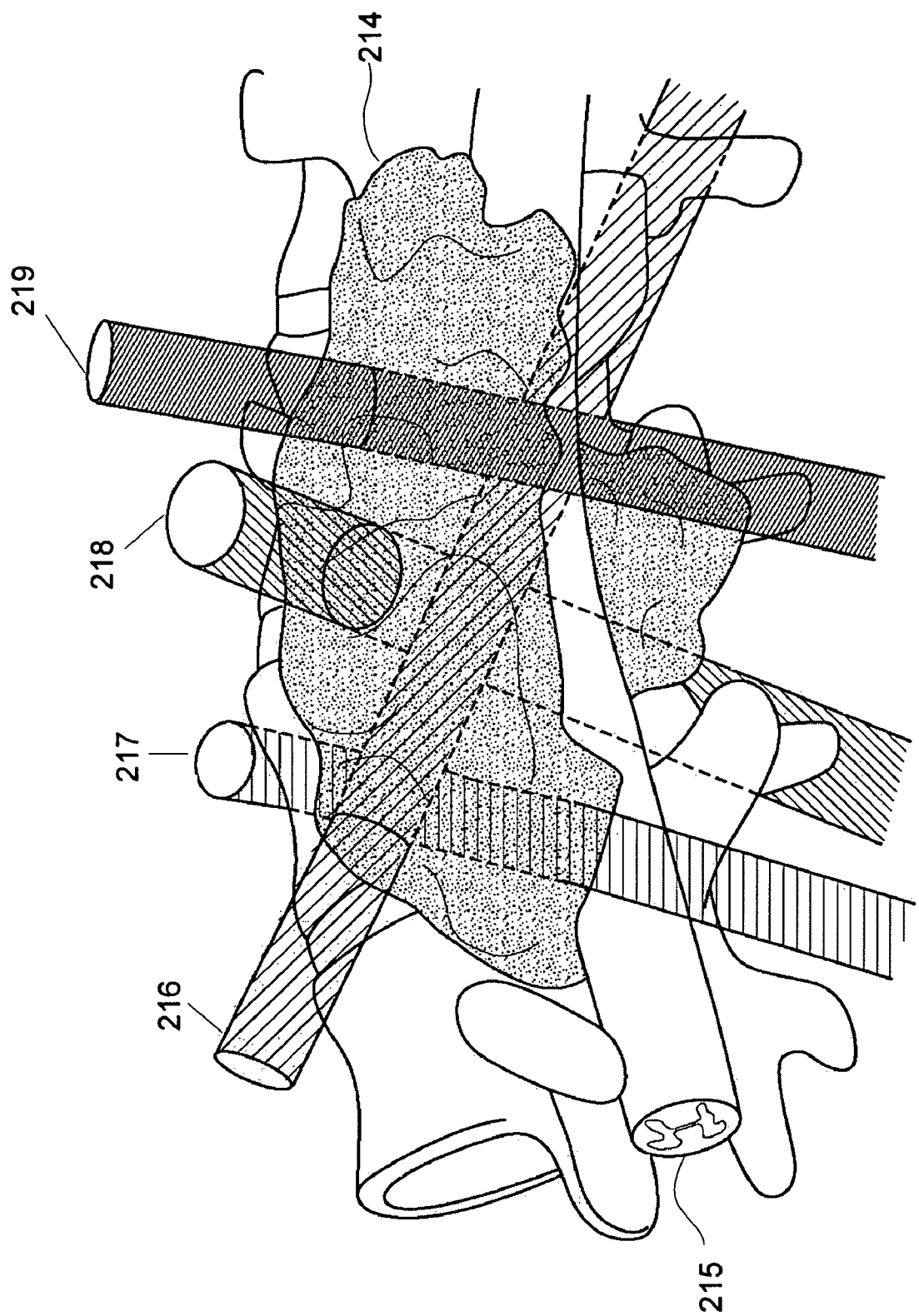
FIG. 2B illustrates one embodiment of image-guide non-isocentric radiation treatment.

FIG. 2A illustrates the configuration of an image-guided, robotic-based radiation treatment system 200 (e.g., the CyberKnife® Radiosurgery System manufactured by Accuray, Inc. of California) in which embodiments of the present invention may be practiced. In FIG. 2A, the radiation treatment source is a linear accelerator (LINAC) 211 mounted on the end of a robotic arm 213 (shown in FIG. 4) having multiple (e.g., 5 or more) degrees of freedom in order to position the LINAC 211 to irradiate a pathological anatomy (target region or volume) in a patient 209 with X-ray treatment beams (e.g., beams 212A, 212B, 212C) delivered from many angles, in many planes, in an operating volume around the patient 209. Treatment may involve beam paths with a single isocenter, multiple isocenters, or with a non-isocentric approach. FIG. 2B illustrates non-isocentric radiation treatment in one embodiment. In FIG. 2B, a pathological anatomy (e.g., a tumor) 214 growing around a spinal cord 215 is treated, for example, by radiation treatment beams 216, 217, 218 and 219, which each intersect the pathological target volume 214 without converging on a single point, or isocenter, within the target.

Returning to FIG. 2A, imaging system 200 may include X-ray sources 201A and 201B and X-ray imagers (detectors) 206A and 206B. The two X-ray sources 201A and 201B may be mounted in fixed positions on the ceiling 207 of an operating room and may be aligned to project imaging X-ray beams 202A and 202B from two different positions, such that imaging axis 203A of beam 202A is substantially parallel with imaging axis 203B of beam 202B, and a ray 204A of beam 202A intersects with a ray 204B of beam 202B at an imaging center (machine isocenter) M, which provides a reference point for positioning the LINAC 211 and the patient 209 on treatment couch 210 during treatment. After passing through the patient 209, imaging X-ray beams 202A and 202B may illuminate respective imaging surfaces of X-ray imagers 206A and 206B, which may be mounted at or near the floor 208 of the operating room and substantially parallel to each other (e.g., within 5 degrees). X-ray imagers 206A and 206B may be substantially coplanar such that the imaging surfaces of X-ray imagers 206A and 206B form a single imaging plane. In one embodiment, X-ray imagers 206A and 206B may be replaced with a single X-ray imager 206 (shown in FIG. 4) with a single imaging plane large enough to capture images produced by both X-ray beams 202A and 202B. As described in greater detail below, radiation treatment system 200 may be configured such that ray 204A intersects ray 204B at an angle substantially less than 90 degrees (e.g., 45 degrees or less). In one embodiment, X-ray beams 202A and 202B may be collimated and/or shaped so that only those portions of the beams which are capable of illuminating the X-ray imagers, such as X-ray beams 205A and 205B, are radiated.

In other embodiments, radiation treatment system 200 may include more or less than two X-ray sources and more or less than two detectors and any of the detectors and/or sources may be movable rather than fixed. In yet other embodiments, the positions of the x-ray sources and the detectors may be interchanged or rotated (e.g., wall mounted such that beams 202A and 202B are substantially horizontal).

The X-ray imagers 206A and 206B may be fabricated from a scintillating material (e.g., amorphous silicon) that converts the X-rays to visible light, and an array of CMOS (complementary metal oxide silicon) or CCD (charge-coupled device) imaging cells (pixels) that convert the light to digital images that can be processed by a digital processing system as described in greater detail below.

In one embodiment, a method for parallel stereovision in an image-guided radiation treatment system includes imaging a three-dimensional (3-D) feature in an imaged volume with two or more imaging X-ray sources having substantially parallel imaging axes, locating the 3-D feature within the imaged volume, and tracking the 3-D feature within the imaged volume by registering the 3-D feature with a 3-D pre-treatment volume study of the imaged volume. Imaging the 3-D feature may include generating substantially parallel X-ray images of the imaged volume which include at least a first X-ray image and a second X-ray image. The first X-ray image may include an image feature corresponding to a 3-D feature within the imaged volume. The second X-ray image may also include an image feature corresponding to the 3-D feature within the imaged volume, and the image feature in the second X-ray image may be substantially similar to the image feature in the first X-ray image. Locating the 3-D feature within the imaged volume may include matching the first image feature with the second image feature to obtain a pair of matched image features, and determining the location of the 3-D feature within the imaged volume from planar coordinates of the pair of matched image features in an imaging plane.

Figure 3:
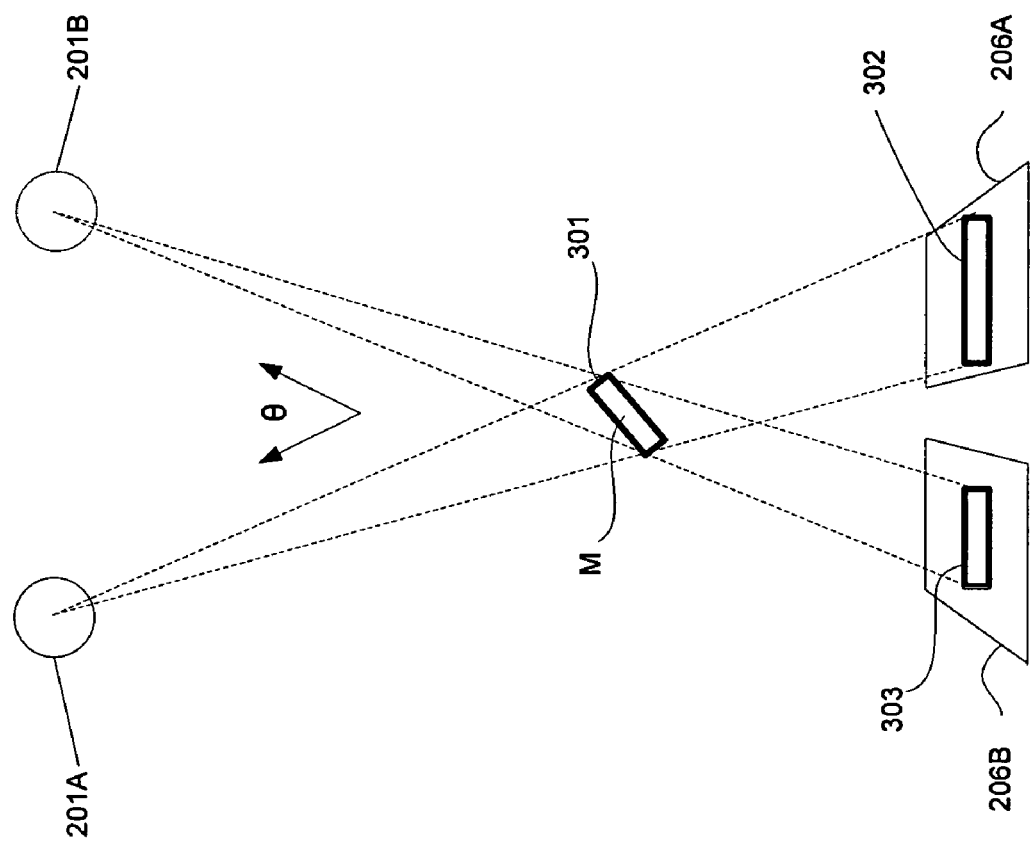
FIG. 3 illustrates one embodiment of parallel stereovision imaging.

FIG. 3 illustrates parallel stereovision imaging in radiation treatment system 200, for example. In FIG. 3, a 3-D anatomical feature 301 (e.g., a bone similar to the bone of FIG. 1), located in the vicinity of imaging center M, is imaged with the two X-ray sources 201A and 201B, and the two X-ray imagers 206A and 206B, subtending an angle $\theta$ at imaging center M that is substantially less than 90 degrees (e.g., less than 45 degrees). Images of anatomical feature 301 are projected in X-ray imagers 206A and 206B. However, unlike the projections illustrated in FIG. 1, the two projections are very similar. Image 302 in X-ray imager 206A is elongated, while image 303 in X-ray imager 206B is foreshortened. However, both images contain features that identify the images as those of the same anatomical object, features that may be recognized, extracted and matched with feature recognition algorithms known in the medical imaging arts (see, e.g., U.S. Pat. No. 5,901,199 by Murphy et al.). As the angle θ is reduced, the range of 3-D feature orientations that produce similar projections in X-ray imager 206A and X-ray imager 206B will increase, increasing the number of image features that may be recognized, extracted and matched. Image features may be anatomical edges, shapes, image gradients, contours, object surfaces, segmented objects or similar anatomical features. Image features may also be created by artificial means such as, for example, placing and/or implanting fiducial markers in the patient.

Figure 4:
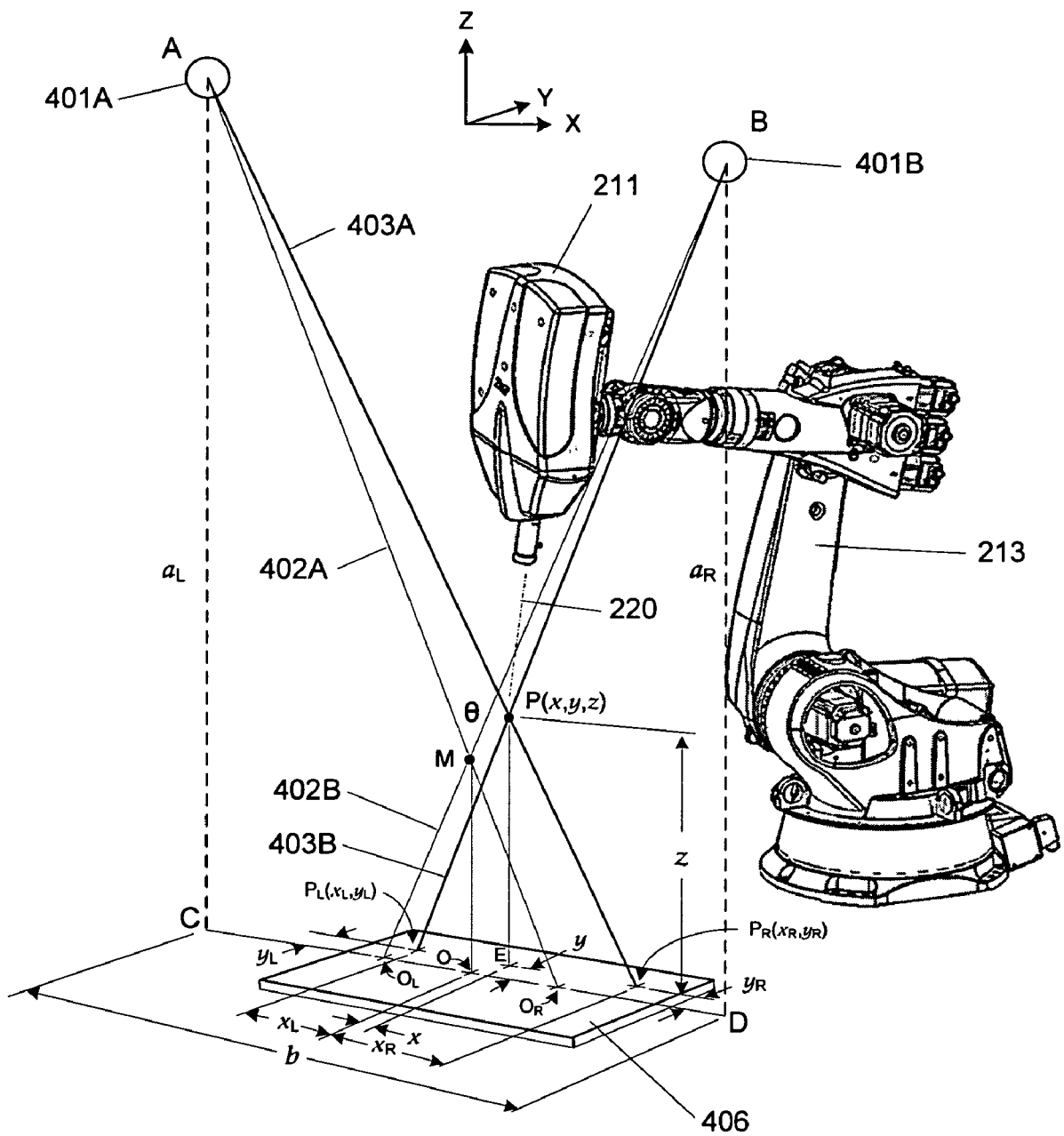
FIG. 4 illustrates one embodiment of image-guided radiation treatment.

FIG. 4 illustrates parallel stereovision geometry in an image-guided radiation treatment system 400, for example. In FIG. 4, LINAC 211 is mounted on robotic arm 213 and is positioned to apply a radiation beam 220 to a point P in the treatment volume. To insure that the point P coincides with a desired point within a pathological anatomy, the in-treatment position of the patient may be registered with a pre-treatment 3-D scan of the patient (e.g., a CT scan) that was used for treatment planning. As described below, parallel stereovision geometry enables 2-D in-treatment X-ray images to be converted directly to 3-D in-treatment position data without using DRRs.

In FIG. 4, X-ray source 401A projects an X-ray beam from point A with a beam axis AC and a ray 402A that passes through imaging center M and intersects imaging plane 406 at a right image center $O_R$, in a right half-plane of imaging plane 406. Similarly, X-ray source 401B projects an X-ray beam from point B with a beam axis BD and a ray 402B that passes through imaging center M, at an angle θ with respect to ray 402A, and intersects the imaging plane 406 at a left image center $O_L$ in a left half-plane of imaging plane 406. A vertical projection (normal to imaging plane 406) from point M to the imaging plane may define an origin O in the imaging plane and an imaging axis OM. X-ray source 401A also projects a ray 403A that passes through point P and intersects the imaging plane of imager 406 at point $P_R$, which may be defined by its displacement $x_R$ in the x-coordinate direction from imaging axis OM, and its displacement $y_R$ in the y-coordinate direction from imaging axis OM. Similarly, X-ray source 401B projects a ray 403B that passes through point P and intersects the imaging plane of imager 406 at point $P_L$, which may be defined by its displacement $x_L$ in the x-coordinate direction from imaging axis OM, and its displacement $y_L$ in the y-coordinate direction from imaging axis OM. The location of point P may be defined by coordinates x,y and z with respect to origin O, where z defines an elevation above imaging plane 406, and x and y define the location of a vertical projection E of point P in imaging plane 406. Every point in an imaged volume subtended by the X-ray beams may be projected in this manner such that one X-ray image of the imaged volume is projected onto the left half-plane (left image) and another substantially similar image is projected onto the right half-plane (right image). In particular, 3-D anatomical features within the imaged volume may be projected as substantially similar image features (e.g., corners, endpoints, curved edges) in the left image and the right image. Radiation treatment system 400 may be further defined by a separation b between X-ray sources 401A and 401B and by the heights $a_L$ and $a_R$ of X-ray sources 401A and 401B, respectively, above imaging plane 406, where the beam axes AC and BD are perpendicular to line segment CD through origin O of imaging plane 406.

Figure 5:
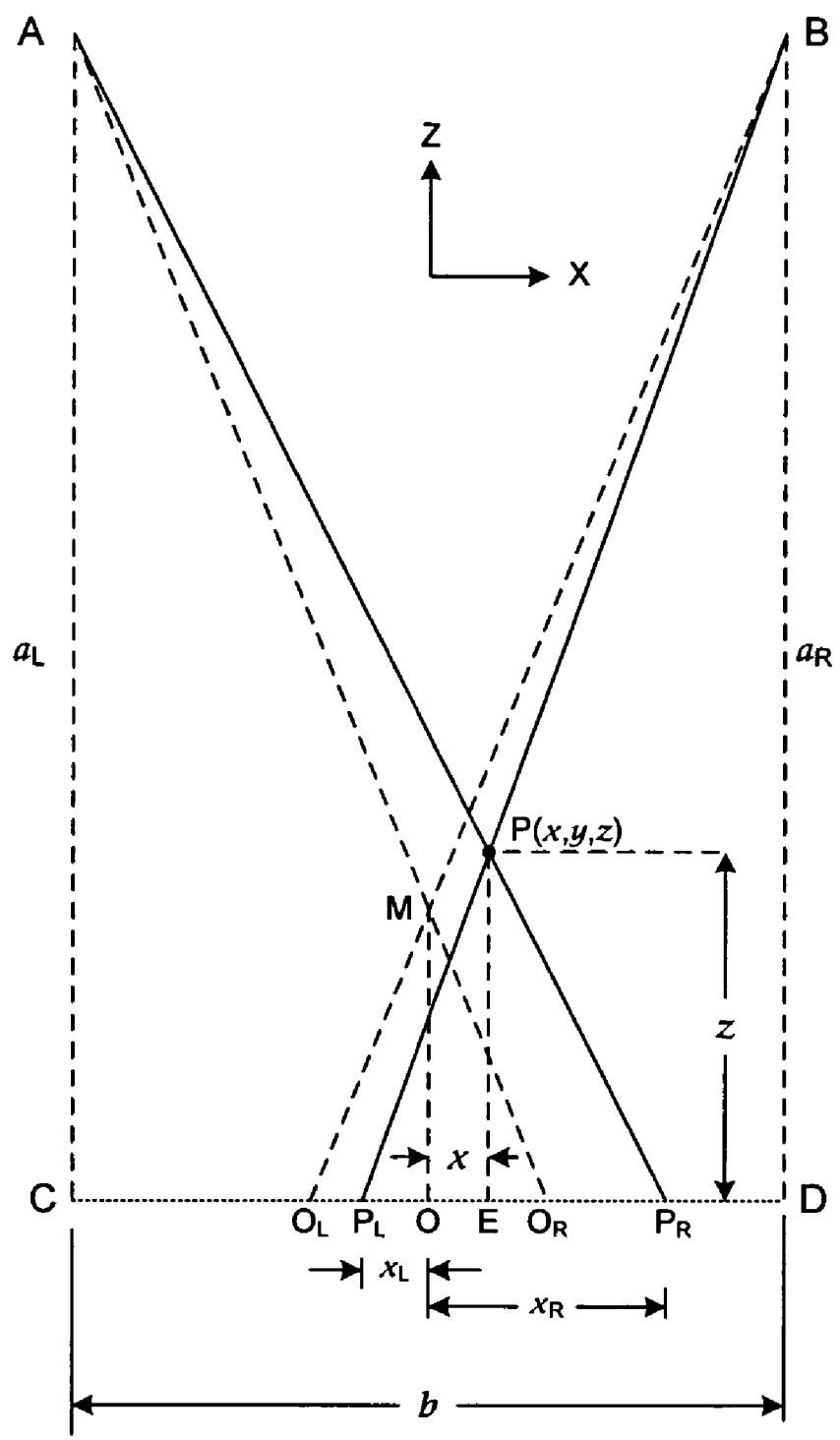
FIG. 5 illustrates a plane view of one embodiment of parallel stereovision geometry.

FIG. 5 illustrates the geometry of the imaging system in radiation treatment system 400, in the X-Z plane. In FIG. 5, triangle $ACP_R$ is similar to triangle $PEP_R$, and triangle $BDP_L$ is similar to triangle $PEP_L$. Similar triangles have similar proportions, therefore:

$$\frac{\overline{CP_R}}{\overline{CA}} = \frac{\overline{EP_R}}{\overline{EP}} \tag{1}$$

and, $$\frac{\overline{DP_L}}{\overline{DB}} = \frac{\overline{EP_L}}{\overline{EP}} \tag{2}$$

where overbars indicate line segments. Accordingly, $$\frac{b/2 + x_R}{a_L} = \frac{x_R - x}{z} \tag{3}$$

and $$\frac{b/2 + x_L}{a_R} = \frac{x_L + x}{z} \tag{4}$$

for the case where $a_L = a_R = a$ (for $a_L \neq a_R$, a calibration factor may be computed as is known in the art), equations (1) and (2) may be added, $$\frac{b + x_R + x_L}{a} = \frac{x_R + x_L}{z} \tag{5}$$

and subtracted, $$\frac{x_R - x_L}{a} = \frac{x_R - x_L - 2x}{z} \tag{6}$$

Letting $\Sigma = x_R + x_L$, and $\Delta = x_R - x_L$, it can be shown that $$z = a\left(\frac{\Sigma}{b + \Sigma}\right) \tag{7}$$

and $$x = \frac{\Delta}{2}\left(1 - \frac{\Sigma}{b + \Sigma}\right) \tag{8}$$

Figure 6:
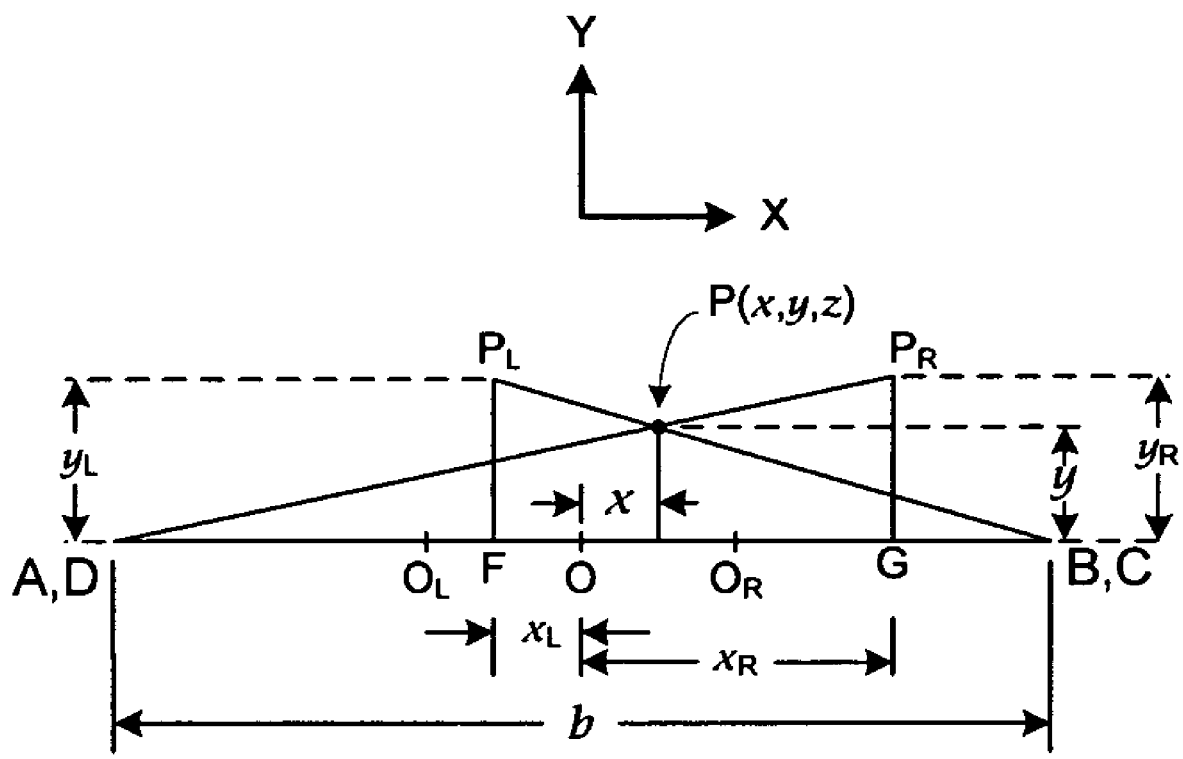
FIG. 6 illustrates another plane view of one embodiment of parallel stereovision geometry.

FIG. 6 illustrates the geometry of the imaging system in radiation treatment system 400, in the X-Y plane. In FIG. 6, point F is the projection of point $P_L$ on the x axis and point G is the projection of point $P_R$ on the x axis. Triangle $AGP_R$ is similar to triangle AEP and triangle $BFP_L$ is similar to triangle PEP. Therefore:

$$\frac{\overline{AG}}{\overline{GP_R}} = \frac{\overline{AE}}{\overline{EP}} \tag{9}$$

and,

-continued $$\frac{\overline{BF}}{\overline{FP_L}} = \frac{\overline{BE}}{\overline{EP}} \qquad (10)$$

Accordingly, there are two independent solutions for y:

$$y_1 = \frac{(b/2 + x)}{(b/2 + x_R)} y_R \qquad (11)$$

and $$y_2 = \frac{(b/2 - x)}{(b/2 + x_L)} y_L \qquad (12)$$

Equations (11) and (12) may be averaged, $$y = \frac{y_1 + y_2}{2} \qquad (13)$$

and solved for y, $$y = \frac{b}{\frac{b/2 + x_R}{y_R} + \frac{b/2 + x_L}{y_L}} \qquad (14)$$

Thus, the 3-D coordinates of point P may be calculated from the planar coordinates of points $P_L$ and $P_R$. Points $P_L$ and $P_R$ may be referred to as a conjugate pair of points corresponding to a 3-D feature point. Any 3-D feature in the imaged volume may be defined in terms of a number of 3-D feature points, which will be projected as an equal number of conjugate pairs of points in imaging plane 406, for example.

In one embodiment, feature extraction and recognition algorithms may be applied to the left image and the right image to extract substantially similar image features from each image. Feature recognition algorithms are known in the art (see e.g., J. B. A. Maintz, M. A. Viergever, "A Survey of Medical Image Registration" *Medical Image Analysis* (1998), Copyright Oxford University Press, Vol. 2, No. 1, pp. 1-37) and, accordingly, are not described in detail. After feature extraction, similarity measures may be applied to the extracted features from each image, and matched as pairs of image features. Similarity measures and matching algorithms for registering 2-D X-ray images with DRR's may be used to match the features extracted. Similarity measures and matching algorithms are known in the art (see, e.g., G. P. Penney, J. Weese, "A comparison of similarity measures for use in 2D-3D medical image registration," IEEE *Trans. Med. Imag.*, vol. 17, pp. 586-595, August 1998) and, accordingly, are not described in detail.

As described above, the image features may not be congruent, but in general will be substantially similar so that features such as corners, endpoints and curved edges of anatomical features may be matched. Once the pairs of image features have been matched, the matched features may be decomposed into conjugate pairs of image points (such as points $P_L$ and $P_R$, for example). When the conjugate pairs of image points for one or more of the matched image features have been determined, the planar coordinates of the conjugate pairs of image points may be mapped to 3-D feature points (such as point P) in the imaged volume, using equations (7), (8) and (14) derived above, to determine the locations of the 3-D features in the imaged volume. In one embodiment, the locations of the 3-D features may be registered directly with 3-D pre-treatment scan data (such as digitized CT scan data, for example) using 3-D transformation algorithms as are known in the art. The 3-D to 3-D registration results may then be used to determine differences between a patient's in-treatment position and the patient's pre-treatment position during diagnostic imaging and/or treatment planning, and to correct for the differences by repositioning the patient and/or modifying the position of radiation treatment source (e.g., LINAC 211).

Figure 7:
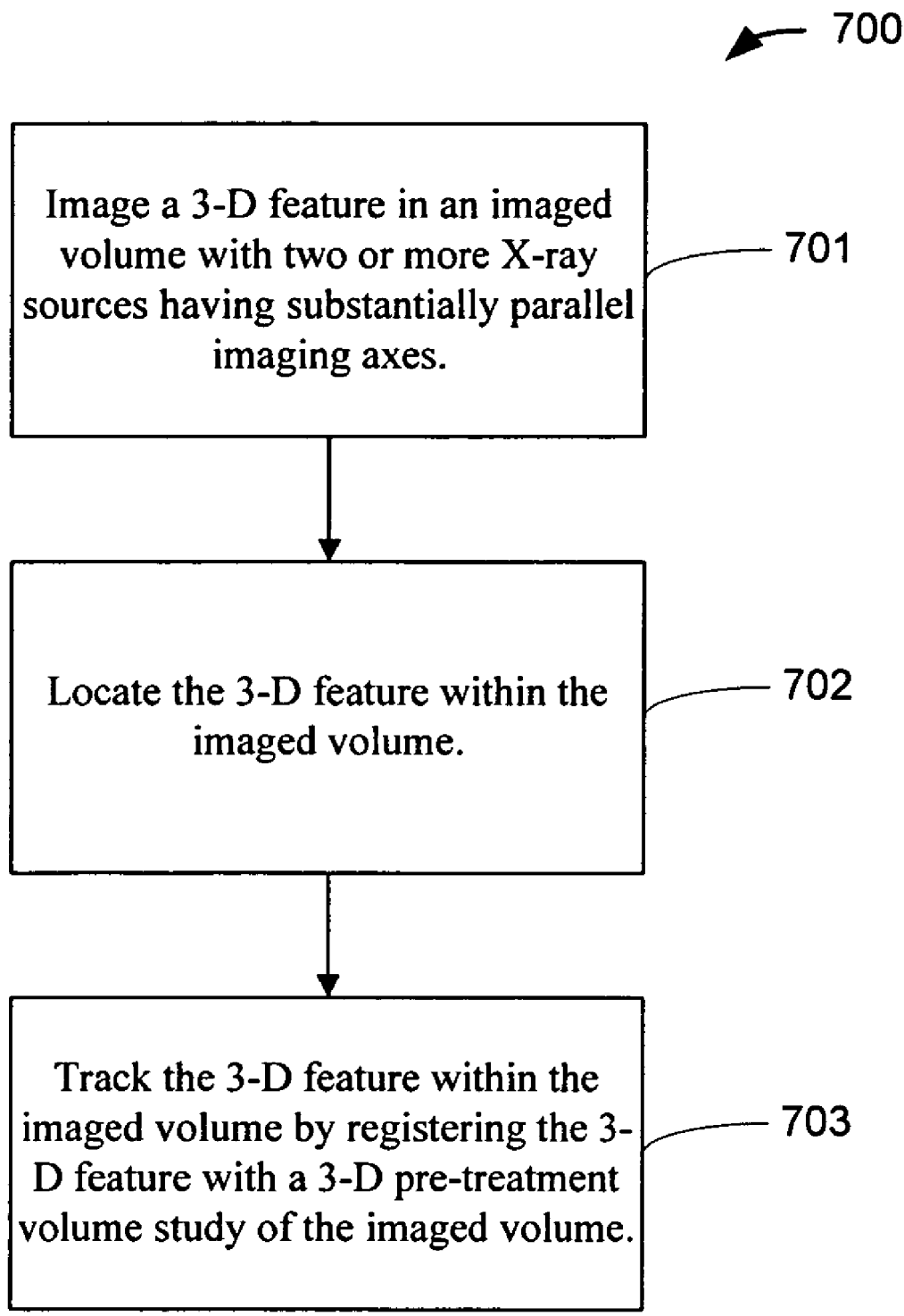
FIG. 7 is a flowchart illustrating one embodiment of a method of parallel stereovision in a radiation treatment system.

Thus, in one embodiment as illustrated in FIG. 7, a method 700 for using parallel stereovision geometry in an image-guided radiation treatment system includes: imaging a 3-D feature within an imaged volume with two or more imaging X-ray sources having substantially parallel imaging axes (step 701); locating the 3-D feature within the imaged volume (step 702); and tracking the 3-D feature within the imaged volume by registering the 3-D feature with a 3-D pre-treatment volume study of the imaged volume (step 703).

Figure 8:
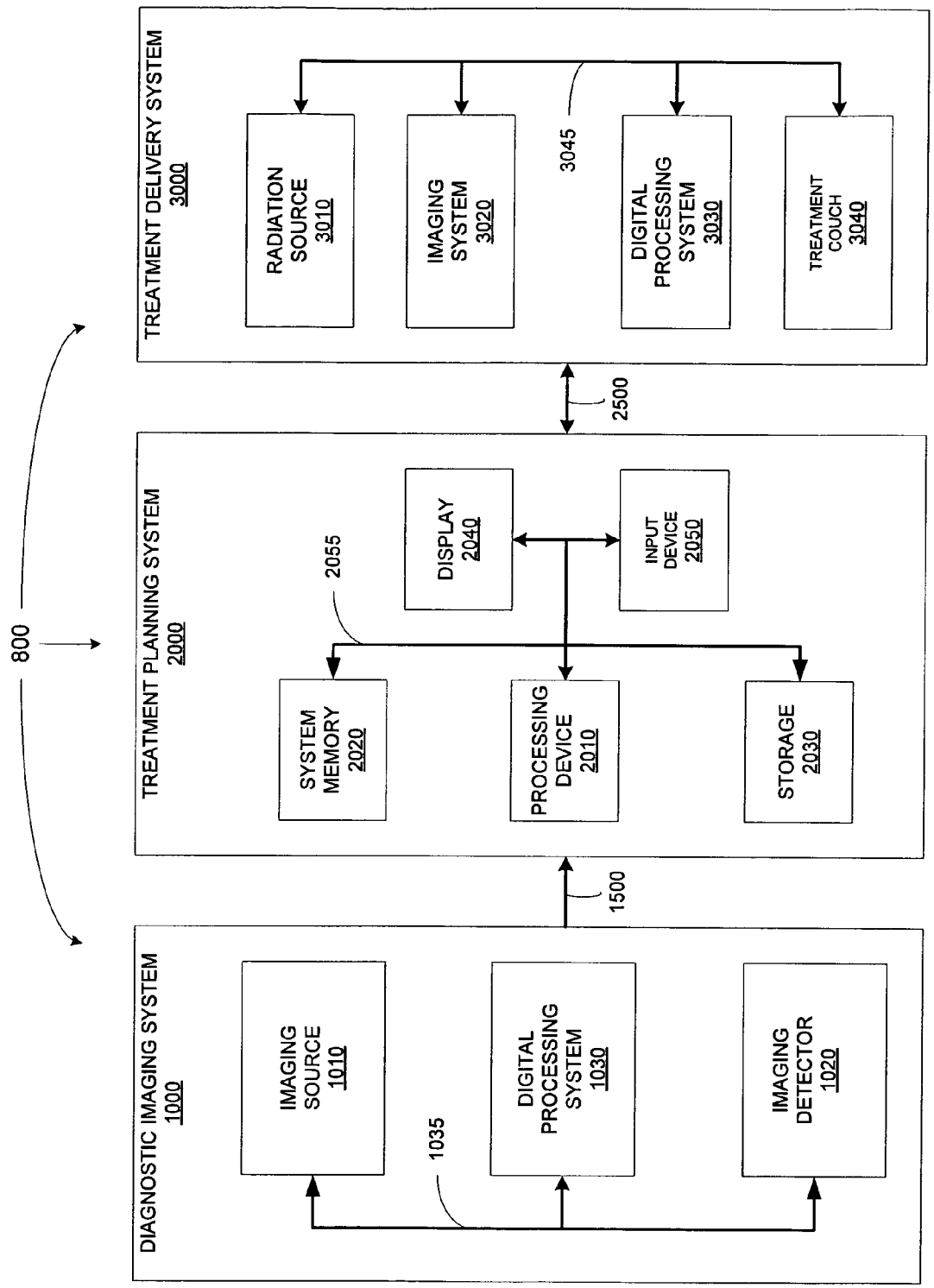
FIG. 8 illustrates a system in which embodiments of the present invention may be implemented.

FIG. 8 illustrates one embodiment of systems that may be used in performing radiation treatment in which features of the present invention may be implemented. As described below and illustrated in FIG. 8, system 800 may include a diagnostic imaging system 1000, a treatment planning system 2000 and a treatment delivery system 3000.

Diagnostic imaging system 1000 may be any system capable of producing medical diagnostic images from a 3-D volume study of a volume of interest (VOI) in a patient, that may be used for subsequent medical diagnosis, treatment planning and/or treatment delivery. For example, diagnostic imaging system 1000 may be a computed tomography (CT) system, a magnetic resonance imaging (MRI) system, a positron emission tomography (PET) system, an ultrasound system or the like. For ease of discussion, diagnostic imaging system 1000 may be discussed below, at times, in terms of a CT imaging modality. However, other imaging modalities such as those above may also be used.

Diagnostic imaging system 1000 includes an imaging source 1010 to generate an imaging beam (e.g., x-rays, ultrasonic waves, radio frequency waves, etc.) and an imaging detector 1020 to detect and receive the beam generated by imaging source 1010, or a secondary beam or emission stimulated by the beam from the imaging source (e.g., in an MRI or PET scan). In one embodiment, diagnostic imaging system 1000 may include one or more diagnostic X-ray sources and one or more corresponding imaging detectors capable of generating 2-D radiographic images, in small angular increments, which may be used to construct 3-D images (e.g., a cone-beam CT scanner). For example, two x-ray sources may be disposed around a patient to be imaged, fixed at an angular separation from each other (e.g., 90 degrees, 45 degrees, etc.) and aimed through the patient toward (an) imaging detector (s) which may be diametrically opposed to the x-ray sources. A single large imaging detector, or multiple imaging detectors, can also be used that would be illuminated by each x-ray imaging source. Alternatively, other numbers and configurations of diagnostic imaging sources and imaging detectors may be used.

The imaging source 1010 and the imaging detector 1020 may be coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor (DSP) or other type of device such as a controller or field programmable gate array (FPGA). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data. Processing device 2010 may represent one or more general-purpose processors (e.g., a microprocessor), special purpose processor such as a digital signal processor (DSP) or other type of device such as a controller, application specific integrated circuit (ASIC) or field programmable gate array (FPGA). Processing device 2010 may be configured to execute instructions for performing treatment planning operations discussed herein.

Treatment planning system 2000 may also include system memory 2020 that may include a random access memory (RAM), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory (ROM) and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein.

Processing device 2010 may also be coupled to a display device 2040, such as a cathode ray tube (CRT) or liquid crystal display (LCD), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as treatment delivery system 3000, so that it may not be necessary to export from the treatment planning system prior to treatment delivery. Treatment planning system 2000 may be linked to treatment delivery system 3000 via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or treatment delivery system 3000 may be in decentralized locations such that the systems may be physically remote from each other. Alternatively, any of diagnostic imaging system 1000, treatment planning system 2000 and/or treatment delivery system 3000 may be integrated with each other in one or more systems.

Treatment delivery system 3000 includes a therapeutic and/or surgical radiation source 3010 to administer a prescribed radiation dose to a target volume in conformance with a treatment plan. Treatment delivery system 3000 may also include an imaging system 3020 to capture in-treatment images of a patient volume (including the target volume) for registration or correlation with the diagnostic images described above in order to position the patient with respect to the radiation source. Imaging system 3020 may include any of the imaging systems described above. Treatment delivery system 3000 may also include a digital processing system 3030 to control radiation source 3010, imaging system 3020 and a patient support device such as a treatment couch 3040. Digital processing system 3030 may be configured to recognize and/or extract anatomical features from 2-D radiographic images from imaging system 3020, from two or more stereoscopic projections, and to determine 3-D coordinates of the anatomical features within the VOI for registration with 3-D scan data generated by processing device 2010 in treatment planning system 2000. Digital processing system 3030 may include one or more general-purpose processors (e.g., a microprocessor), special purpose processor such as a digital signal processor (DSP) or other type of device such as a controller, application specific integrated circuit (ASIC) or field programmable gate array (FPGA). Digital processing system 3030 may also include other components (not shown) such as memory, storage devices, network adapters and the like. Digital processing system 3030 may be coupled to radiation source 3010, imaging system 3020 and treatment couch 3040 by a bus 3045 or other type of control and communication interface.

Digital processing system 3030 may implement methods (e.g., such as method 700 described above) to register images obtained from imaging system 3020 with pre-operative treatment planning images in order to align the patient on the treatment couch 3040 within the treatment delivery system 3000, and to precisely position the radiation source with respect to the target volume.

The treatment couch 3040 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 3040 may be a component of another mechanical mechanism, such as the Axum® treatment couch developed by Accuray, Inc. of California, or be another type of conventional treatment table known to those of ordinary skill in the art.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

It will be apparent from the foregoing description that aspects of the present invention may be embodied, at least in part, in software. That is, the techniques may be carried out in a computer system or other data processing system in response to its processor, such as processing device 2010 or digital processing system 3030, executing sequences of instructions contained in a memory, such as system memory 2020. In various embodiments, hardware circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as processing device 2010 or digital processing system 3030.

A machine-readable medium can be used to store software and data which when executed by a data processing system causes the system to perform various methods of the present invention. This executable software and data may be stored in various places including, for example, system memory 2020 and storage 2030 or any other device that is capable of storing software programs and/or data.

Thus, a machine-readable medium includes any mechanism that provides (i.e., stores and/or transmits) information in a form accessible by a machine (e.g., a computer, network device, personal digital assistant, manufacturing tool, any device with a set of one or more processors, etc.). For example, a machine-readable medium includes recordable/non-recordable media (e.g., read only memory (ROM); random access memory (RAM); magnetic disk storage media; optical storage media; flash memory devices; etc.), as well as electrical, optical, acoustical or other forms of propagated signals (e.g., carrier waves, infrared signals, digital signals, etc.); etc.

It should be appreciated that references throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention. In addition, while the invention has been described in terms of several embodiments, those skilled in the art will recognize that the invention is not limited to the embodiments described. The embodiments of the invention can be practiced with modification and alteration within the scope of the appended claims. The specification and the drawings are thus to be regarded as illustrative instead of limiting on the invention.

What is claimed is:

1. A method in an image-guided radiation treatment system, comprising:
    imaging a 3-D feature in an imaged volume with two or more in-treatment imaging X-ray sources having substantially parallel imaging axes, wherein imaging the 3-D feature comprises:
        generating a first X-ray image of the imaged volume comprising a first image feature corresponding to the 3-D feature within the imaged volume; and
        generating a second X-ray image substantially parallel to the first X-ray image, comprising a second image feature corresponding to the 3-D feature within the imaged volume, wherein the second image feature is substantially similar to the first image feature; and
    locating the 3-D feature within the imaged volume.

2. The method of claim 1, further comprising tracking the 3-D feature within the imaged volume by registering the 3-D feature with a 3-D pre-treatment volume study of the imaged volume.

3. The method of claim 1, wherein locating the 3-D feature comprises:
    matching the first image feature with the second image feature to obtain a pair of matched image features; and
    determining a location of the 3-D feature within the imaged volume from planar coordinates of the pair of matched image features.

4. The method of claim 1, wherein the first image feature in the first X-ray image comprises a first plurality of image points and the second image feature in the second X-ray image, substantially similar to the first image feature, comprises a second plurality of image points, and wherein matching the image features comprises computing a similarity measure between the first image feature and the second image feature and matching the first plurality of image points with the second plurality of image points in a plurality of conjugate pairs of image points.

5. The method of claim 4, wherein determining the location of the 3-D feature within the imaged volume comprises mapping the plurality of conjugate pairs of image points to the plurality of feature points of the 3-D feature within the imaged volume.

6. The method of claim 1, wherein the 3-D feature within the imaged volume comprise one of a fiducial marker, a curved edge, a corner and an endpoint.

7. A method in an image-guided radiation treatment system, comprising:

imaging a 3-D feature in an imaged volume with two or more in-treatment imaging X-ray sources having substantially parallel imaging axes; and locating the 3-D feature within the imaged volume, wherein the 3-D feature comprises a plurality of feature points, and wherein generating the first X-ray image and the second X-ray image comprises, for each feature point:

generating a first image point in an imaging plane by projecting a first X-ray through the feature point in the imaged volume from a first X-ray source, the first image point having a first set of planar coordinates in the imaging plane defined by a first displacement from an imaging axis in a first direction and a second displacement from the imaging axis in a second direction; and generating a second image point in the imaging plane by projecting a second X-ray through the feature point in the imaged volume from a second X-ray source, the second image point having a second set of planar coordinates in the imaging plane defined by a third displacement from the imaging axis in the first direction and a forth displacement from the imaging axis in the second direction, the first image point and the second image point comprising a conjugate pair of image points corresponding to the feature point.

8. A system, comprising:
a stereoscopic imaging system comprising a first imaging device having a first imaging axis and a second imaging device having a second imaging axis substantially parallel to the first imaging axis, to image a 3-D feature within an imaged volume; and a processing device coupled with the imaging system, wherein the processing device is configured to locate the 3-D feature within the imaged volume, wherein to image the 3-D feature the imaging system is configured to generate substantially parallel X-ray images of the imaged volume comprising a first X-ray image and a second X-ray image, the first X-ray image including a first image feature corresponding to a 3-D feature within the imaged volume, the second X-ray image including a second image feature corresponding to the 3-D feature within the imaged volume, wherein the second image feature is substantially similar to the first image feature.

9. The system of claim 8, wherein the processing device is further configured to track the 3-D feature within the imaged volume by registering the 3-D feature with a 3-D pre-treatment volume study of the imaged volume.

10. A system, comprising:
a stereoscopic imaging system comprising a first imaging device having a first imaging axis and a second imaging device having a second imaging axis substantially parallel to the first imaging axis, to image a 3-D feature within an imaged volume; and a processing device coupled with the imaging system, wherein the processing device is configured to locate the 3-D feature within the imaged volume, wherein to locate the 3-D feature the processing device is configured to match the first image feature with the second image feature to obtain a pair of matched image features and to determine a location of the 3-D feature within the imaged volume from planar coordinates of the pair of matched image features.

11. The system of claim 10, wherein the first image feature in the first X-ray image comprises a first plurality of image points and the second image feature in the second X-ray image, substantially similar to the first image feature, comprises a second plurality of image points, and wherein to match the image features the processing device is configured to compute a similarity measure between the first image feature and the second image feature and to match the first plurality of image points with the second plurality of image points in a plurality of conjugate pairs of image points.

12. The system of claim 11, wherein to determine the location of the 3-D feature within the imaged volume, the processing device is configured to map the plurality of conjugate pairs of image points to the plurality of feature points of the 3-D feature in the imaged volume.

13. The system of claim 10, wherein the 3-D feature in the imaged volume comprises one of a fiducial marker, a curved edge, a corner and an endpoint.

14. The system of claim 10, wherein the first and second imaging devices are diagnostic imaging devices.

15. The system of claim 14, wherein the first image feature and the second imaged feature are an anatomical feature within a patient.

16. A system, comprising:
a stereoscopic imaging system comprising a first imaging device having a first imaging axis and a second imaging device having a second imaging axis substantially parallel to the first imaging axis, to image a 3-D feature within an imaged volume; and a processing device coupled with the imaging system, wherein the processing device is configured to locate the 3-D feature within the imaged volume, wherein the 3-D feature comprises a plurality of feature points, and wherein to generate the substantially parallel X-ray images, the processing device is further configured, for each feature point, to:

generate a first image point in an imaging plane by projecting a first X-ray through the feature point in the imaged volume from a first X-ray source, the first image point having a first pair of planar coordinates in the imaging plane defined by a first displacement from an imaging axis in a first direction and a second displacement from the imaging axis in a second direction; and to generate a second image point in the imaging plane by projecting a second X-ray through the feature point in the imaged volume from a second X-ray source, the second image point having a second pair of planar coordinates in the imaging plane defined by a third displacement from the imaging axis in the first direction and a forth displacement from the imaging axis in the second direction, the first image point and the second image point comprising a conjugate pair of image points corresponding to the feature point.

17. The system of claim 16, wherein the first X-ray and the second X-ray subtend an angle at the feature point less than approximately forty-five degrees.

18. An article of manufacture comprising a machine-accessible medium including data that, when accessed by a machine, cause the machine to perform operations, comprising:

imaging a 3-D feature in an imaged volume with two or more in-treatment imaging X-ray sources having substantially parallel imaging axes, wherein imaging the feature comprises:

generating a first X-ray image of the imaged volume comprising a first image feature corresponding to a 3-D feature within the imaged volume; and generating a second X-ray image substantially parallel to the first X-ray image, comprising a second image feature corresponding to the 3-D feature within the imaged volume, wherein the second image feature is substantially similar to the first image feature; and locating the 3-D feature within the imaged volume.

19. The article of manufacture of claim 18, wherein the machine-accessible medium further includes data that cause the machine to perform operations, comprising tracking the 3-D feature within the imaged volume by registering the 3-D feature with a 3-D pre-treatment volume study of the imaged volume.

20. The article of manufacture of claim 18, wherein locating the feature comprises:

matching the first image feature with the second image feature to obtain a pair of matched image features; and determining a location of the 3-D feature within the imaged volume from planar coordinates of the pair of matched image features.

21. The article of manufacture of claim 20, wherein the first image feature in the first X-ray image comprises a first plurality of image points and the second image feature in the second X-ray image, substantially similar to the first image feature, comprises a second plurality of image points, and wherein matching the image features comprises computing a similarity measure between the first image feature and the second image feature and matching the first plurality of image points with the second plurality of image points in a plurality of conjugate pairs of image points.

22. The article of manufacture of claim 21, wherein determining the location of the 3-D feature within the imaged volume comprises mapping the plurality of conjugate pairs of image points to the plurality of feature points of the 3-D feature within the imaged volume.

23. The article of manufacture of claim 18, wherein the 3-D feature comprises a plurality of feature points, and wherein generating the first X-ray image and the second X-ray image comprises, for each feature point:

generating a first image point in an imaging plane by projecting a first X-ray through the feature point in the imaged volume from a first X-ray source, the first image point having a first set of planar coordinates in the imaging plane defined by a first displacement from an imaging axis in a first direction and a second displacement from the imaging axis in a second direction; and generating a second image point in the imaging plane by projecting a second X-ray through the feature point in the imaged volume from a second X-ray source, the second image point having a second set of planar coordinates in the imaging plane defined by a third displacement from the imaging axis in the first direction and a forth displacement from the imaging axis in the second direction, the first image point and the second image point comprising a conjugate pair of image points corresponding to the feature point.

24. The article of manufacture of claim 18, wherein the 3-D feature within the imaged volume comprise one of a fiducial marker, a curved edge, a corner and an endpoint.

25. An apparatus, comprising:

means for imaging a 3-D feature in an imaged volume with two or more in-treatment imaging X-ray sources having substantially parallel imaging axes, wherein the means for imaging the 3-D feature comprises:

means for generating a first X-ray image of an imaged volume, comprising a first image feature corresponding to a 3-D feature within the imaged volume; and means for generating a second X-ray image substantially parallel to the first image feature, comprising a second image feature corresponding to the 3-D feature within the imaged volume, wherein the second image feature is substantially similar to the first image feature; and means for locating the 3-D feature within the imaged volume.

26. The apparatus of claim 25, further comprising means for tracking the 3-D feature within the imaged volume by registering the 3-D feature with a 3-D pre-treatment volume study of the imaged volume.

27. The apparatus of claim 25, wherein locating the 3-D feature comprises:

means for matching the first image feature with the second image feature to obtain a pair of matched image features; and means for determining a location of the 3-D feature within the imaged volume from planar coordinates of the pair of matched image features.

28. The apparatus of claim 25, further comprising means for registering the location of the 3-D feature with a 3-D scan of the imaged volume.

* * * * *